United States Patent [19]
Jiskoot et al.

[11] Patent Number: 5,413,002
[45] Date of Patent: May 9, 1995

[54] LIQUID SAMPLER

[75] Inventors: Mark A. Jiskoot, Wells; Barry R. Baker, Kent, both of United Kingdom

[73] Assignee: Jiskoot Autocontrol Limited, Kent, United Kingdom

[21] Appl. No.: 77,361

[22] Filed: Jun. 17, 1993

[30] Foreign Application Priority Data

Jul. 2, 1992 [GB] United Kingdom .............. 9214154.8

[51] Int. Cl.6 .............................................. G01N 1/00
[52] U.S. Cl. ............................................... 73/863.03
[58] Field of Search ............ 73/863.02, 863.03, 863.31, 73/863.33, 863.81, 863.83, 863.84, 863.85

[56] References Cited

U.S. PATENT DOCUMENTS

| | | | |
|---|---|---|---|
| 3,546,945 | 12/1970 | Collins | 73/863.02 |
| 3,757,583 | 9/1973 | Ludewig, Jr. | 73/863.33 |
| 4,116,067 | 9/1978 | Pankratz et al. | 73/863.31 |
| 4,454,772 | 6/1984 | Brunner et al. | 73/863.86 |
| 4,517,849 | 5/1985 | Nakahori et al. | 73/863.31 |
| 5,101,670 | 4/1992 | Steger et al. | 73/863.03 |

FOREIGN PATENT DOCUMENTS

| | | | |
|---|---|---|---|
| 0570875 | 11/1961 | Belgium | 73/863.02 |
| 868105 | 2/1953 | Germany | 73/863.81 |
| 2635380 | 2/1978 | Germany | 73/863.03 |
| 0684376 | 9/1979 | U.S.S.R. | 73/863.03 |

*Primary Examiner*—Robert Raevis
*Attorney, Agent, or Firm*—Burns, Doane, Swecker & Mathis

[57] ABSTRACT

A sampler for flowing liquid in, for example, a pipeline, said sampler comprising, a pump assembly situated, in use, within the flowing liquid, sampling means connected to said pump assembly to provide a sample of said liquid, drive means to operate said pump assembly, said drive means including driver means, mounted, in use, within said flowing liquid to be driven by the flowing liquid, whereby flowing liquid drives the driver means which in turn drives the drive means and the pump assembly.

15 Claims, 5 Drawing Sheets

LIQUID SAMPLER

BACKGROUND OF THE INVENTION

The present invention relates to liquid samplers.

Apparatus for sampling liquids are well known. They are frequently provided to sample liquids in, for example, a pipeline.

Although the invention is not restricted to the following use, samplers for bunker fuel oil are particularly difficult to design. The reason for this is that bunker fuel for ships tends to be of very low quality and generally comprises the residue of the oil after the more usable parts have been removed mixed with diesel fuel. The fuel oil tends to be very waxy and, indeed, unless it is kept hot may solidify.

It is desirable to sample bunker fuel as it is being loaded into a ship because it's constituents can vary and it is common to sample such bunker fuel so as to determine it's constituents for future analysis. It is common practice for three samples to be kept in separate containers, one by the ship owner, one by the fuel supplier, and one for retention for later analysis/arbitration if so required.

A known arrangement of sampler comprises a valve mechanism which is rotated, rotation of the valve mechanism selectivety pas, sing a sample of liquid within the pipeline to three sampling jars, the rotation of the valve being carried out by a drive system driven by means of a propeller within the pipeline so that the propeller rotates in accordance with the flow of bunker fuel and the amount of bunker fuel collected, therefore, is in some way dependent upon the amount of bunker fuel passed along the pipeline. Such an arrangement is useful particularly in that it does not require an outside power supply (which is highly desirable in the somewhat explosive environment that the sampler operates).

However there are some difficulties, particularly caused by the fact that the bunker fuel tends to be waxy and solidify.

SUMMARY AND OBJECTS

The present invention provides a sampler for flowing liquid in, for example, a pipeline, said sampler comprising:

a pump assembly situated within the flowing liquid for pumping the liquid under pressure;

sampling means connected to said pump assembly to provide a sample of said liquid;

drive means to operate said pump assembly, said drive means including means, such as a propeller mean, mounted within said flowing liquid to be driven by the flowing liquid;

said drive means being coupled to said driven means such that a rate of providing liquid samples is proportional to a rate at which the liquid is flowing in the pipeline;

whereby the flowing liquid drives driven the means which in turn drives the drive means and the pump assembly.

By utilising power from the propeller driven by the liquid in the pipeline, the apparatus is self sufficient and does not require an outside power source. The use of one or more propellers assists in mixing the liquid being sampled.

The apparatus is provided with the pump assembly within the pipeline which thereby keeps the pump assembly warm and so that positive pressure is applied to the liquid to discharge the liquid outside the pipeline and this reduces the possibility of blockage due to the sampled liquid solidifying.

The sampler may include a columnar member for insertion into the pipeline through a side aperture, and may include a plate means to close the side aperture. The drive means may comprise a shaft extending from the propeller into a housing outside the pipeline, and the housing may mount a variable reduction gearbox, the output of the reduction gearbox driving a camshaft. The camshaft may drive direct, or via a rocker, a shaft which extends down to the pump assembly and thereby operates the pump assembly. The pump assembly may include a liquid inlet, whereby liquid within the pipeline may flow into the pump assembly, and check valves to eject liquid out of the pipeline to the sampling means under the control of the camshaft.

BRIEF DESCRIPTION OF THE DRAWINGS

Liquid samplers providing preferred arrangements of the invention will now be described by way of example only and with reference to the accompanying drawings in which.

DETAILED DESCRIPTION OF PREFERRED EMBODIMENTS

Figure 1:
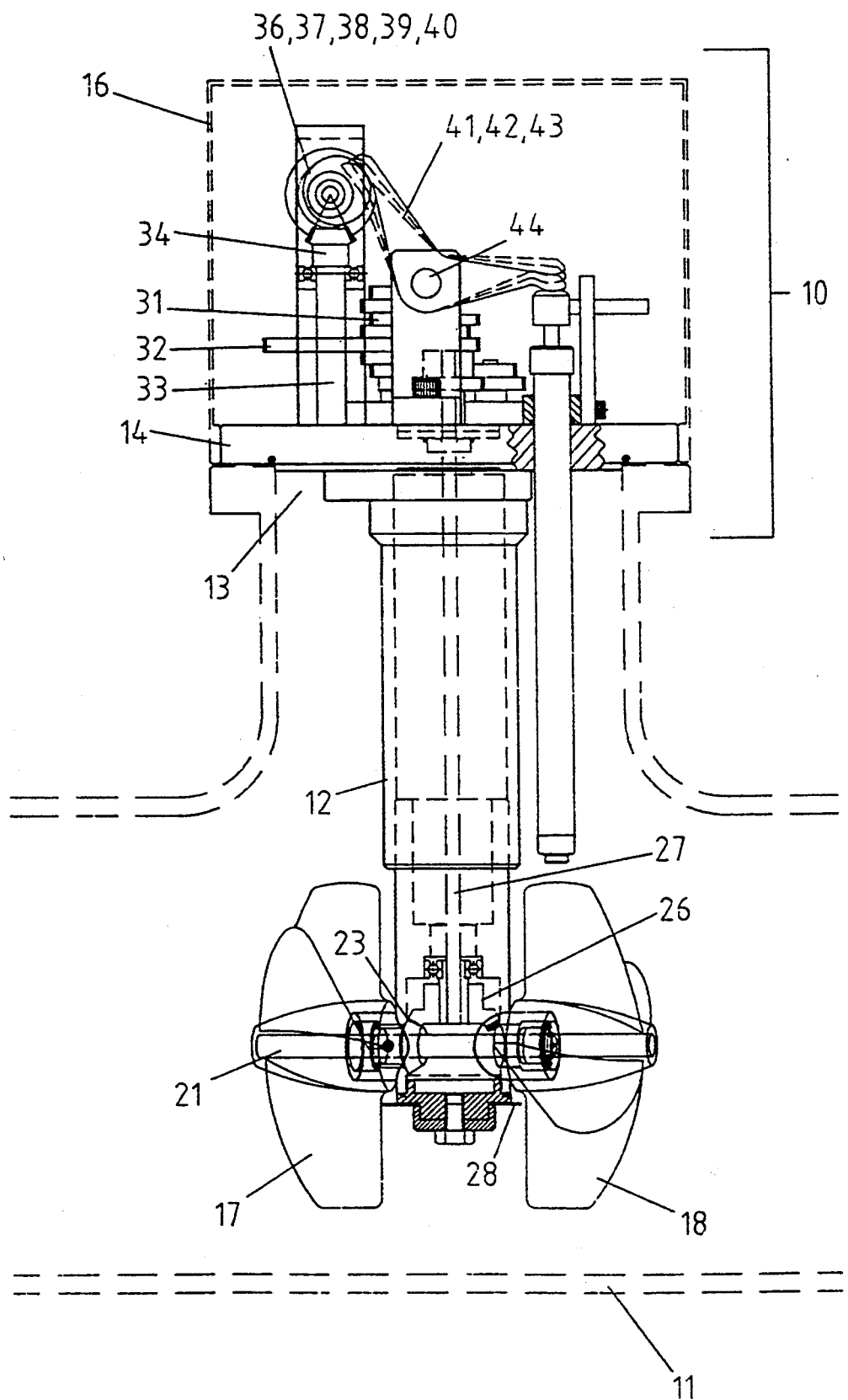
FIG. 1 is a side view of a first sampler according to the invention.
Figure 2:
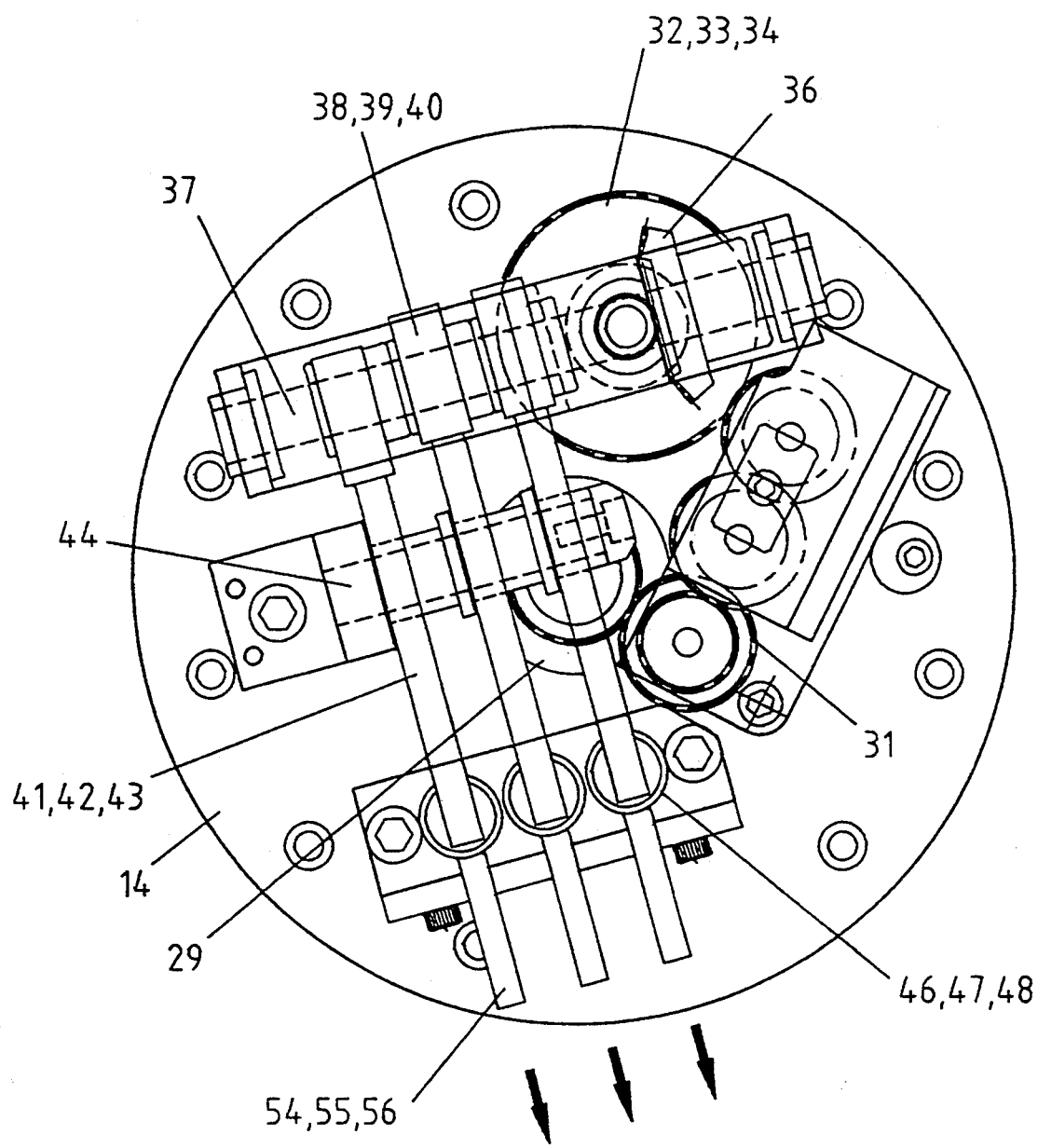
FIG. 2 is a plan view of the sampler of FIG. 1.
Figure 3:
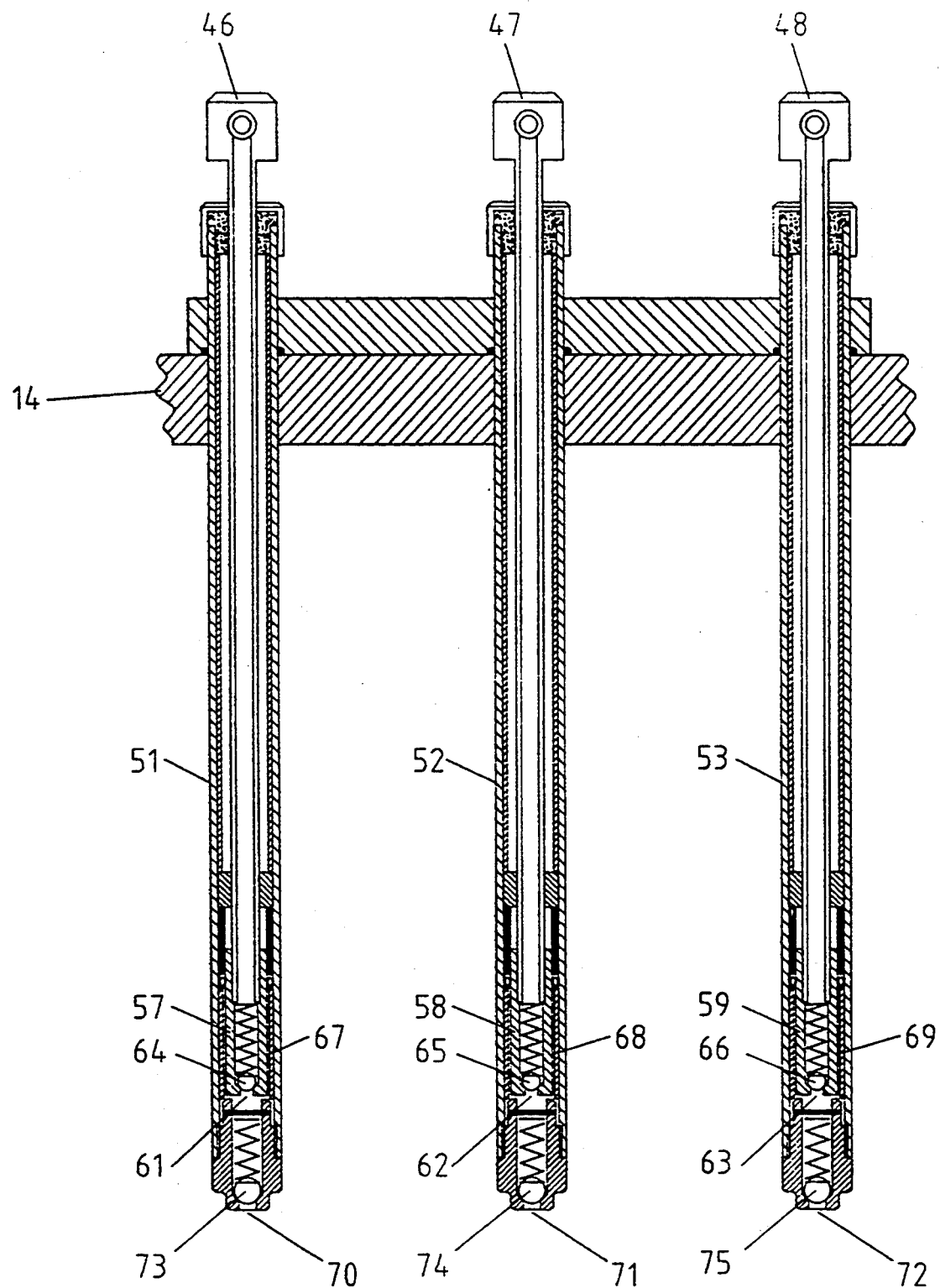
FIG. 3 is a enlarged section of the pump assembly of FIG. 1.

Referring to FIG. 1 there is shown a side view of a bunker fuel oil sampler 10 mounted in a pipeline 11. The sampler 10 comprises a columnar member 12 which extends into the pipeline 11 through an aperture 13, a flange plate 14 of the sampler 10 closing off the aperture 13. Mounted to the flange plate 14 outside the pipeline 11 is a housing 16 which encloses part of a drive system.

The lower end of the columnar member to mounts, on each side thereof, a respective propeller 17,18, the propellers being mounted on a single bearing mounted shaft 21. The axis of the propellers 17,18 are arranged to be generally coaxial with the longitudinal axis of the pipeline 11. The middle of shaft 21 mounts a bevel gear 23 which meshes with a bevel gear 26 attached to the lower end of a bearing mounted vertical shaft 27 which runs up the columnar member 12.

Mounted to the lower most point of the columnar member 12 is a plate 28 which forms a flow straightener between the propellers 17,18 to increase the power output of the device.

The vertical shaft 27 passes up through the flange plate 14 and mounts at its upper end a spur gear 29. The spur gear 29 meshes with a reduction gear train 31 mounted on the flange plate 14. The out put of the reduction gear train 31 is passed to a gear 32 mounted on an upright bearing mounted shaft 33 carrying at its upper end a bevel gear 34; the bevel gear 34 meshes with a bevel gear 36 forming part of a horizontal camshaft 37, the camshaft 37 including three cams 38,39,40 against which bear three rockers 41,42,43 mounted to a rocker shaft 44. The fingers of the rockers 41-43 opposite the cams 38-40 bear on the top end of three hollow tappets 46-48 which extend downwardly through the flange plate 14 and through three downwardly depending tubular members 51-53.

Three sample ejector pipes 54-56 are provided connected to the top end of the hollow tappets 46,47,48, and each connecting with the interior of respective hollow tappets 46-48.

The lower end of each tubular member 51-53 carries a hollow piston 57-59. Each hollow piston member 57-59 includes an end bore 61-63 closed by a spring loaded check valve 64-66, and reciprocates in a closed chamber 67-69 at the lower end of the tubular member 51-53. The closed chambers 67-69 each include a bore 70-72 in the lower end thereof closed by a spring loaded check valve 73-75, the bores 70-72 being situated adjacent one of the propellers 18.

In use, therefore, the bunker fuel oil sampler 10 is mounted in a pipeline 11 via an aperture 13 with a flange plate 14 closing of the aperture 13, Bunker fuel oil passing through the pipeline 11 drives the propellers 17,18, the action of the propellers 17,18 to an extent mixing the fuel oil. The speed of rotation of the propellers 17,18 is generally dependent on the speed of fuel oil through the pipeline 11.

Rotation of the propellers 17,18 is transmitted via shaft 21 and bevel gear 23 to the vertical shaft 27 which is thereby rotated. The vertical shaft 27 drives the reduction gear train 31 which via the gear 32 and shaft 33 drives the camshaft 37. As the camshaft 37 rotates, the cams 38,39,40 which are at 120° intervals around the axis of the camshaft 37, rock in succession rockers 41,42,43. Thus in succession the rockers 41,42,43 depress the hollow tappets 46,47,48. As each hollow tappet 46-48 is depressed, liquid in the respective closed chamber 67 is compressed against the check valve 64-66 and thereby flows up the respective hollow tappet and out, under pressure, to the respective ejector pipe 54-56.

As the hollow tappet 46-48 rises after the ejection stroke, the relevant check valve 73-75 opens and bunker fuel oil passes through the respective bore 70m72 into the closed chamber 67-69.

The arrangements of gears in the reduction gear train 31 may be amended so as to change the overall reduction gear ratio to suit the desired relative rate of sampling to flow of liquid.

The propellers 17,18 may be made of a heat aged plastic material. This material is particularly resilient but if a solid member passes along the pipeline, as can happen, then the blades of the propeller will break in preference to damage being caused the remainder of the sampler apparatus. The propellers may be easily replaced.

In addition to the above, there may be provided a temperature indicator in the form of a temperature sensor adjacent the sampler apparatus with a limit stop which provides both the current and maximum temperature experienced during flow. An intrinsically safe water alarm may be provided which will be set to stop operation of the sampler at a predetermined percentage water content of the oil. This is based on measuring the dielectric constant of the fluid and may be mounted on the sampler.

There may be provided an intrinsically safe counter for indication of the total flow and number of samples taken and this may be provided by a magnet mounted on the cam shaft passing a reed switch on the housing of the sampler.

A second sampler apparatus according to the invention now be described with references to FIGS. 4 and 5. In this embodiment, similar parts carry similar reference numerals and we will only describe the major differences between the two embodiments.

In principle, the main difference is that the second sampler apparatus includes a gear selector mechanism whereby the gear selection ratio may be readily changed.

In principle, the gear 32 is mounted to the shaft 33 in such a way that it may be disposed at different vertical position to engage different gears in the reduction gear train 31, and in order to arrange this change of gear simply, the reduction gear train 31 may be pivoted away from its normal position in which it engages the gear 32 to a position in which allows the gear 32 to be moved vertically. axially.

Figure 4:
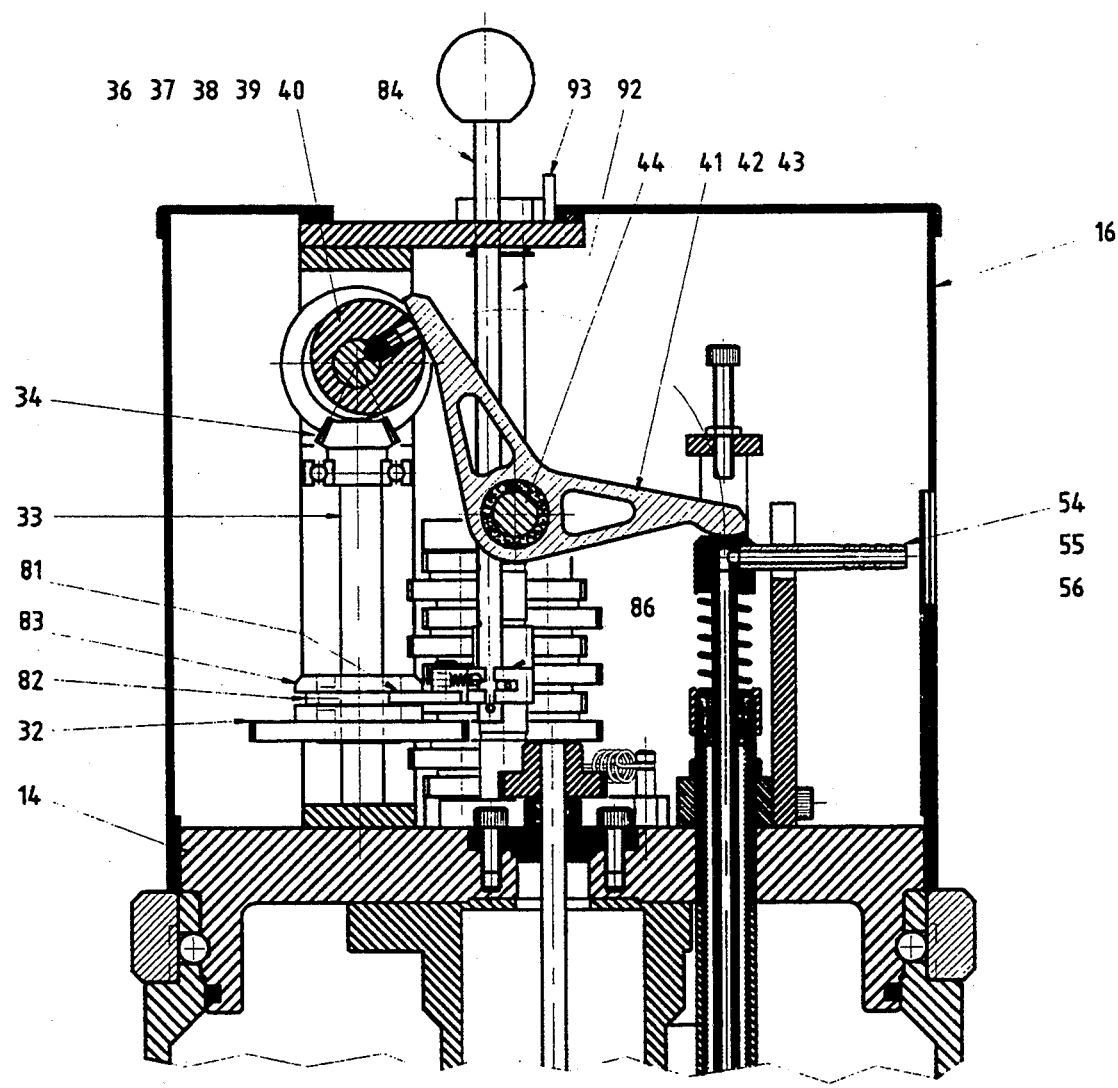
FIG. 4 is a partial vertical section of a second sampler according to the invention, and, FIG. 5 is a horizontal section of the sampler of FIG. 4.
Figure 5:
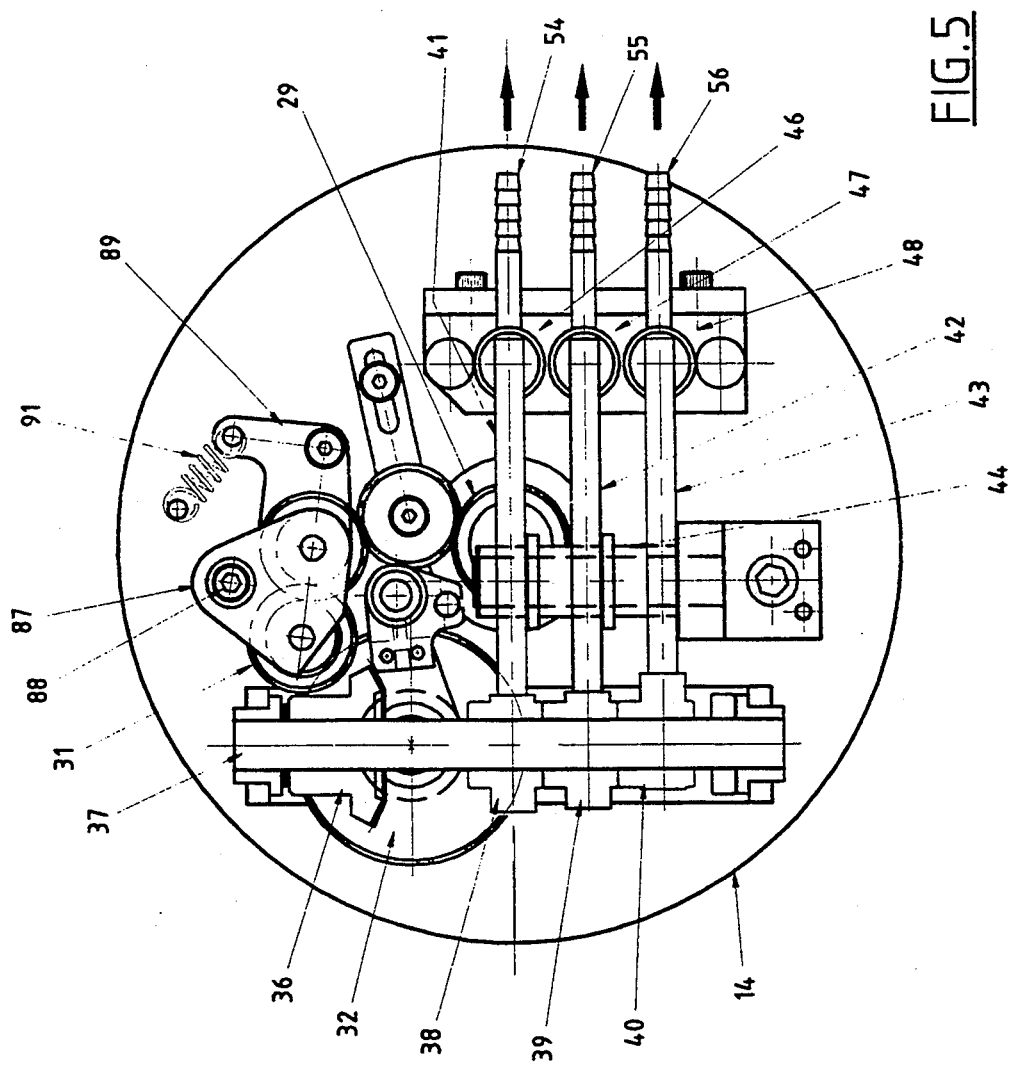

Referring to FIGS. 4 and 5 it will be seen that the gear 32 is mounted to the shaft 33, and may be moved up and down the shaft 33 by a finger 81 engaging in an annular groove 82 in a sleeve 83 attached,to the gear 32. The finger 81 is mounted to be moved vertically by means of a vertical rod 84 which protrudes from the housing 16. There is provided a ball detent mechanism 86 which only allows the rod 84 to properly engage in predetermined vertical positions which correspond to different vertical positions for the gear 32 to engage different sets of gears in the reduction gear-train 31.

In order to allow the vertical movement of the gear 32, the reduction gear train 31 is mounted on a frame 87 pivotally mounted about a pivot 88. A bell crank 89 and spring 91 urge the reduction gear train 31 into engagement with the gear 32, there being provided a vertical rod which extends from the housing 16 with a lever 93 to physically rotate the frame 87 so to disengage the reduction gear train 31 from the gear 32 against the pressure of the spring 91.

Thus in use, when it is desired to change the relative gearing between the propellers 17,18 and cams 41,42,43, (for example when a large load of oil is to be measured, collecting a large number of samples would be undesirable) one pivots the lever §3 to thereby pivot rod 92 and frame 87 so as to disengage the reduction gear train 31 from the gear 32. The gear 32 is then lifted or lowered by means of the rod 84 to a position in which it will engage the relevant gear in the reduction gear train 31, which position is determined by engagement of the ball-detent mechanism 86. The lever 93 then returns to its normal position so that the reduction gear train 31 and gear 32 reengage.

The invention is not restricted to the details of the foregoing example. Clearly other numbers of samples may be taken.

A downstream fixed or spring loaded restriction may be provided to generate backpressure sufficient to ensure the priming of the pumps, the restriction is so controlled so as to ensure that a minimum present pressure is experienced by the pumps at all times.

In another arrangement a quick coupling arrangement such as that used in quick release fluid couplings may be employed instead of bolting around the main flange plate, thereby allowing for the working mechanism to be easily removed or replaced so that the mount piece may be permanently located and the working mechanism removed and transported.

A sampler apparatus as described may be used in other circumstances, for example, sampling other liquids such as oils that are in the petrochemical industry known as "black" and also "white" oils namely both unrefined and refined.

We claim:

1. A sampler for sampling liquid flowing in a pipeline, said sampler comprising:

a pump assembly situated within the flowing liquid for pumping the liquid under pressure;

sampling means connected to said pump assembly to provide a sample of said liquid; and drive means to operate said pump assembly, said drive means including driven means including a propeller mounted within said flowing liquid to be driven by the flowing liquid, said drive means including a shaft extending from the propeller into a housing outside the pipeline;

said drive means being coupled to said driven means such that a rate of providing liquid samples is proportional to a rate at which the liquid is flowing in the pipeline;

whereby the flowing liquid drives the driven means which in turn drives the drive means and the pump assembly.

2. A sampler as claimed in claim 1 in which the housing mounts a variable reduction gearbox, the output of the reduction gearbox being connected to drive a camshaft, the camshaft being connected to drive a shaft which extends down to the pump assembly and thereby operates the pump assembly.

3. A sampler as claimed in claim 2, in which there are provided a plurality of pump assemblies and sampling means whereby a plurality of separate samples of said liquid may be collected.

4. A sampler as claimed in claim 1 in which the pump assembly includes a liquid inlet, whereby liquid within the pipeline may flow into the pump assembly, and check valves to eject liquid out of the pipeline to the sampling means under the control of the camshaft.

5. A sampler as claimed in claim 4, in which there are provided a plurality of pump assemblies and sampling means whereby a plurality of separate samples of said liquid may be collected.

6. A sampler as claimed in claim 1 in which there are provided three pump assemblies to provide three separate samples of said liquid.

7. A sampler as claimed in claim 1 including a columnar member for insertion into the pipeline through a side aperture, and a plate means to close the side aperture.

8. A sampler as claimed in claim 7, in which there are provided a plurality of pump assemblies and sampling means whereby a plurality of separate samples of said liquid may be collected.

9. A sampler as claimed in claim 1, in which there are provided a plurality of pump assemblies and sampling means whereby a plurality of separate samples of said liquid may be collected.

10. A sampler for sampling liquid flowing in a pipeline, said sampler comprising:

a plurality of pump assemblies situated within the flowing liquid;

a sampling means connected to each of said pump assemblies to provide a sample of said liquid;

drive means to operate said pump assemblies, said drive means including driven means including a propeller mounted within said flowing liquid to be driven by the flowing liquid, the drive means including a shaft extending from the propeller into a housing outside the pipeline;

whereby flowing liquid drives the driven means which in turn drives the drive means which in turn sequentially activates each of the pump assemblies.

11. A sampler as claimed in claim 10 in which the housing mounts a variable reduction gearbox, the output of the reduction gearbox being connected to drive a camshaft, the camshaft being connected to drive a shaft which extends down to the pump assemblies and thereby operates the pump assemblies.

12. A sampler as claimed in claim 11 in which each of the pump assemblies includes a liquid inlet, whereby liquid within the pipeline may flow into each of the pump assemblies, and check valves to eject liquid out of the pipeline to the sampling means under the control of the camshaft.

13. A sampler as claimed in claim 10 including a columnar member for insertion into the pipeline through a side aperture, and a plate means to close the side aperture.

14. A sampler as claimed in claim 10 in which the housing mounts a variable reduction gearbox, the output of the reduction gearbox being connected to drive a camshaft, the camshaft being connected to drive a shaft which extends down to the pump assemblies and thereby operates the pump assemblies.

15. A sampler as claimed in claim 14 in which each of the pump assemblies includes a liquid inlet, whereby liquid within the pipeline may flow into each of the pump assemblies, and check valves to eject liquid out of the pipeline to the sampling means under the control of the camshaft.

* * * * *